(12) United States Patent
Kronja

(10) Patent No.: US 7,186,240 B1
(45) Date of Patent: Mar. 6, 2007

(54) SAFETY NEEDLE ASSEMBLY

(76) Inventor: Ivan Kronja, 3375 Foot Hill Rd. #614, Carpinteria, CA (US) 93013

( * ) Notice: Subject to any disclaimer, the term of this patent is extended or adjusted under 35 U.S.C. 154(b) by 0 days.

(21) Appl. No.: 11/261,798

(22) Filed: Oct. 31, 2005

(51) Int. Cl.
*A61M 5/32* (2006.01)
(52) U.S. Cl. .................. 604/198; 604/192
(58) Field of Classification Search .......... 604/198, 604/263, 197, 110, 192, 164.08
See application file for complete search history.

(56) References Cited

U.S. PATENT DOCUMENTS

| | | | |
|---|---|---|---|
| 5,116,325 A | * | 5/1992 | Paterson ............ 604/192 |
| 5,312,369 A | | 5/1994 | Arcusin et al. |
| 5,490,841 A | | 2/1996 | Landis |
| 5,868,716 A | | 2/1999 | Sweeney et al. |
| 5,913,846 A | * | 6/1999 | Szabo ............ 604/263 |
| 6,120,482 A | | 9/2000 | Szabo |
| D469,179 S | | 1/2003 | Nakagami et al. |
| 2003/0078548 A1 | | 4/2003 | Kobayashi |

* cited by examiner

*Primary Examiner*—Nicholas D. Lucchesi
*Assistant Examiner*—Laura Bouchelle

(57) ABSTRACT

A safety needle assembly for locking over a hypodermic needle to inhibit inadvertent contact with the hypodermic needle includes a tube being configured to receive an end of the syringe and being in fluid communication with the syringe. A hypodermic needle is fluidly coupled to and extending away from the tube. A cap is selectively positioned over and covering the hypodermic needle. The cap is positioned in either a covered position or an exposed position. The covered position is defined by the cap being positioned over a portion of the tube and a free end of the hypodermic needle to inhibit access to the hypodermic needle. The exposed position is defined by the cap being positioned away from the hypodermic needle to expose the free end of the hypodermic needle.

6 Claims, 3 Drawing Sheets

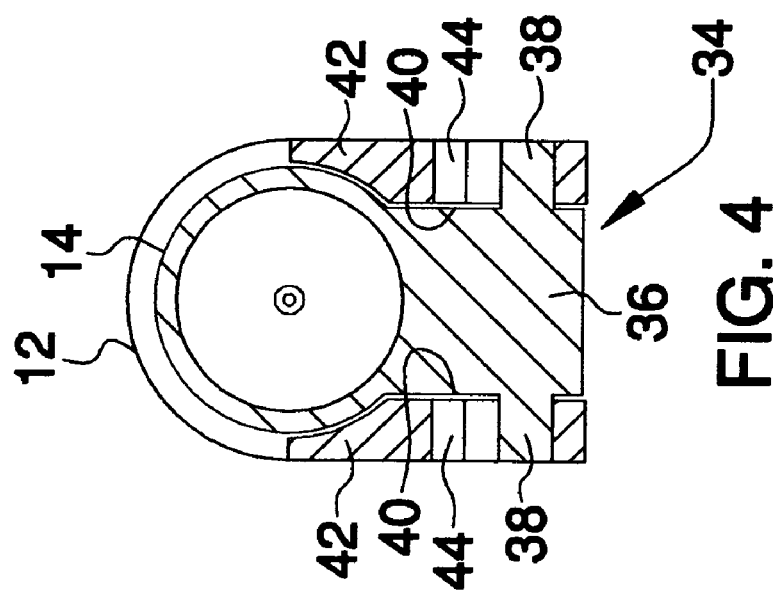
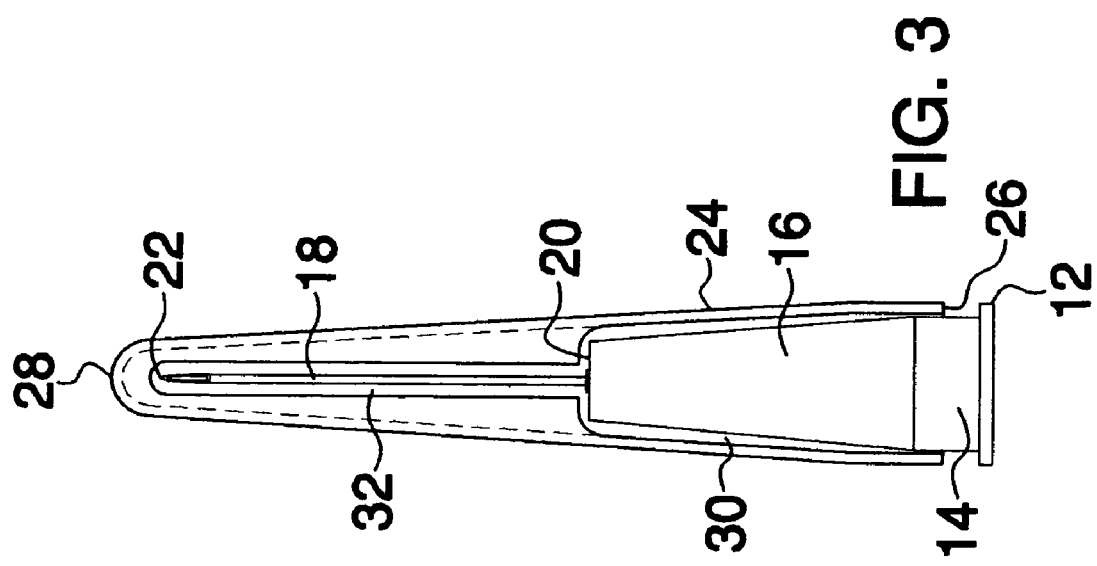

SAFETY NEEDLE ASSEMBLY

BACKGROUND OF THE INVENTION

1. Field of the Invention

The present invention relates to hypodermic needle guards and more particularly pertains to a new hypodermic needle guard for locking over a hypodermic needle to inhibit inadvertent contact with the hypodermic needle.

2. Description of the Prior Art

The use of hypodermic needle guards is known in the prior art. U.S. Pat. No. 5,312,369 describes a device for being selectively positioned over a hypodermic needle to limit access to the hypodermic needle. Another type of hypodermic needle guard is U.S. Pat. No. 6,120,482 for selectively covering a hypodermic needle to avoid accidental sticks and prevent contamination of the hypodermic needle.

While these devices fulfill their respective, particular objectives and requirements, the need remains for a device that includes certain improved features allowing the cap to be secured in a position over the hypodermic needle and inhibit the inadvertent exposure of the hypodermic needle.

SUMMARY OF THE INVENTION

The present invention meets the needs presented above by generally comprising a tube being configured to receive an end of the syringe and being in fluid communication with the syringe. A hypodermic needle is fluidly coupled to and extending away from the tube. A cap is selectively positioned over and covers the hypodermic needle. The cap is positioned in either a covered position or an exposed position. The covered position is defined by the cap being positioned over a portion of the tube and a free end of the hypodermic needle to inhibit access to the hypodermic needle. The exposed position is defined by the cap being positioned away from the hypodermic needle to expose the free end of the hypodermic needle.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a bottom view of the present invention with the cap in the covered position.

FIG. 4 is a cross-sectional view of the present invention taken along line 4—4 of FIG. 1.

DESCRIPTION OF THE PREFERRED EMBODIMENT

Figure 1:
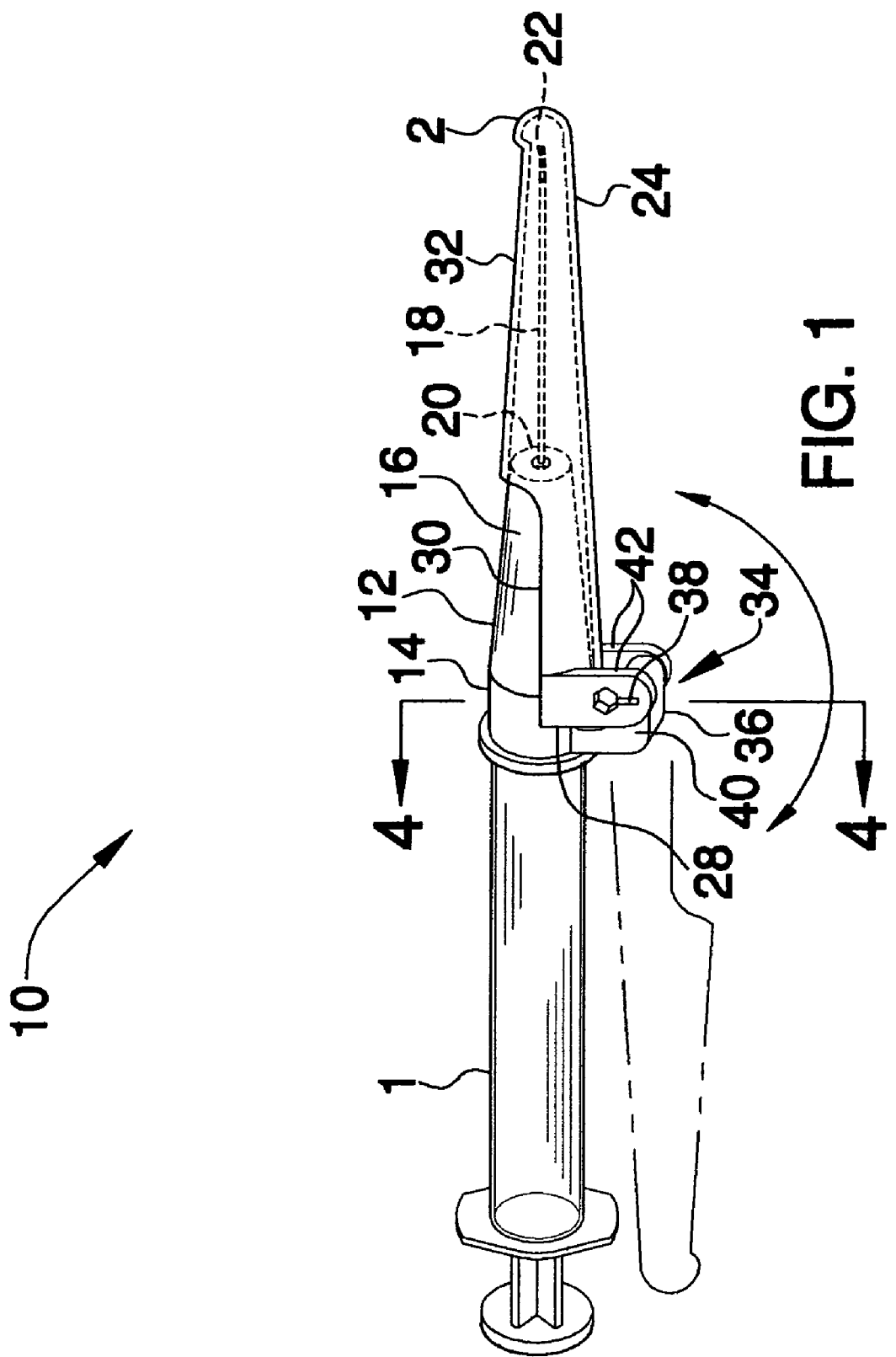
FIG. 1 is a perspective view of a safety needle assembly according to the present invention.
Figure 2:
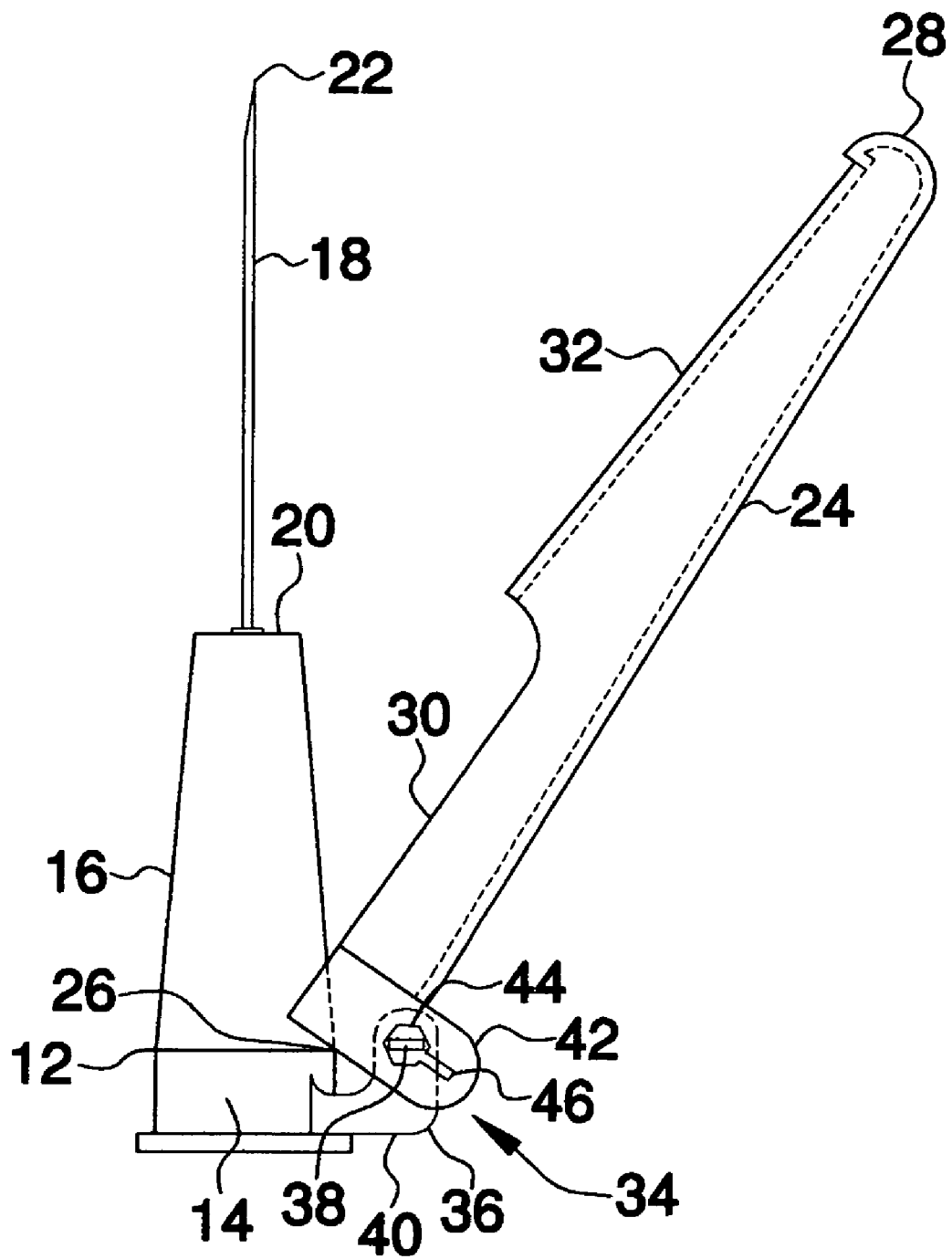
FIG. 2 is a side view of the present invention with the hypodermic needle exposed.

With reference now to the drawings, and in particular to FIGS. 1 through 4 thereof, a new hypodermic needle guard embodying the principles and concepts of the present invention and generally designated by the reference numeral 10 will be described.

As best illustrated in FIGS. 1 through 4, the safety needle assembly 10 generally comprises a tube 12 being configured to receive an end of a syringe 1 and is in fluid communication with the syringe 1. The tube 12 includes a base portion 14 and a transfer portion 16. The base portion 14 is configured to engage the end of the syringe 1 and fluidly couple the transfer portion 16 to the syringe 1.

A hypodermic needle 18 is fluidly coupled to and extends away from a distal end 20 of the transfer portion 16 with respect to the base portion 14. A free end 22 of the hypodermic needle 18 is configured to pierce a skin of a person and to permit fluid communication between the syringe 1, the transfer portion 16 of the tube 12 and the person.

A cap 24 is selectively positioned over and covers the hypodermic needle 18 to inhibit the hypodermic needle 18 from inadvertently penetrating a person. The cap 24 is positioned in either a covered position or an exposed position. The covered position is defined by the cap 24 being positioned over a portion of the tube 12 and a free end 22 of the hypodermic needle 18 to inhibit access to the hypodermic needle 18. The exposed position is defined by the cap 24 being positioned away from the hypodermic needle 18 to expose the free end 22 of the hypodermic needle 18. The cap 24 includes a first end 26 removably coupled to the tube 12 and a second end 28 extending beyond the free end 22 of the hypodermic needle 18 in a direction away from the tube 12 when the cap 24 is in the covered position. The cap 24 has a channel 30 therein positioned adjacent to the first end 26 and has a size and shape configured to receive a portion of the tube 12 when the cap 24 is in the covered position. The cap 24 has an elongated needle slot 32 therein extending from the channel 30 and towards the second end 28. The hypodermic needle 18 slot receives the hypodermic needle 18 to permit the cap 24 to extend substantially around the hypodermic needle 18 and restrict access to the hypodermic needle 18 when the cap 24 is pivoted into the covered position.

A hinge 34 is coupled between the tube 12 and the cap 24 to permit pivoting of the cap 24 with respect to the tube 12. The hinge 34 includes a stanchion 36 being integrally coupled to the base portion 14 of the tube 12 and extending substantially orthogonally outwardly from the tube 12. The hinge 34 further includes a pair of pivot plates 38 extending outwardly from sides 40 of the stanchion 36 and extending substantially perpendicular to a longitudinal axis of the tube 12. The hinge 34 also includes a pair of arms 42 being integrally coupled to the cap 24 adjacent the first end 26 of the cap 24. The arms 42 are positioned in a spaced relationship to permit the stanchion 36 to be positioned between the arms 42. Each of the arms 42 has an aperture 44 extending therethrough. Each of the pivot plates 38 extends through one of the aperture 44s to permit the arms 42 to pivot around the pivot plates 38 and thereby allow the cap 24 to pivot with respect to the tube 12. Each of the arms 42 includes a locking slot 46 extending therethrough. Each of the locking slots 46 extends into one of the apertures 44. Each of the locking slots 46 receives one of the pivot plates 38 when the cap 24 is in the closed position to inhibit rotation of the cap 24 and inadvertently exposing the hypodermic needle 18 when the cap 24 is in the covering position.

In use, the user pivots the cap 24 to the exposed position and thereby exposes the hypodermic needle 18. The free end 22 of the hypodermic needle 18 is then inserted into the person and the syringe 1 is used to transfer the fluids between the person and the syringe 1. Once the transfer of fluids is complete the free end 22 of the hypodermic needle 18 is removed from the person. The cap 24 is then rotated to the covered position and the pivot plates 38 are pressed into the locking slot 46 of each of the arms 42 to secure the cap 24 in the covered position and inhibit the cap 24 being inadvertently pivoted and exposing the hypodermic needle 18.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A safety needle assembly for use on a syringe, said assembly comprising:
    a tube being configured to receive an end of the syringe and being in fluid communication with the syringe;
    a hypodermic needle being fluidly coupled to and extending away from said tube; and
    a cap being selectively positioned over and covering said hypodermic needle, said cap being positioned in either a covered position or an exposed position, said covered position being defined by said cap being positioned over a portion of said tube and a free end of said hypodermic needle to inhibit access to said hypodermic needle, said exposed position being defined by said cap being positioned away from said hypodermic needle to expose said free end of said hypodermic needle;
    a hinge being coupled between said tube and said cap to permit pivoting of said cap with respect to said tube, said hinge including
        a stanchion being integrally coupled to said tube and extending substantially orthogonally outwardly from said tube;
        a pair of pivot plates extending outwardly from sides of said stanchion and extending substantially perpendicular to a longitudinal axis of said tube, said plates lying in a plane orientated approximately perpendicular to a longitudinal axis of said hypodermic needle,
        a pair of arms being integrally coupled to said cap, said arms being positioned in a spaced relationship to permit said stanchion to be positioned between said arms, each of said arms having an aperture extending therethrough, each of said pivot plates extending through one of said apertures to permit said arms to pivot around said pivot plates and thereby allow said cap to pivot with respect to said tube, each of said arms includes a locking slot extending therethrough, each of said locking slots extending into one of said apertures, each of said locking slots receiving one of said pivot plates when said cap is in said closed position to inhibit rotation of said cap and inadvertently exposing said hypodermic needle when said cap is in said covering position, said arms being moved toward said longitudinal axis of said hypodermic needle and toward said tube such that said plates align with and are received by an associated one of said locking slots.

2. The assembly of claim 1, wherein said tube includes a base portion and a transfer portion, said base portion being configured to engage the end of the syringe and fluidly couple said transfer portion to the syringe.

3. The assembly of claim 2, wherein said hypodermic needle is fluidly coupled to and extending away from a distal end of said transfer portion with respect to said base portion.

4. The assembly of claim 1, wherein said cap includes a first end removably coupled to said tube and a second end extending beyond said free end of said hypodermic needle in a direction away from said tube when said cap is in said covered position, said cap having a channel therein positioned adjacent to said first end and having a size and shape configured to receive a portion of said tube when said cap is in said covered position.

5. The assembly of claim 4, wherein said cap has an elongated needle slot therein extending from said channel and towards said second end, said hypodermic needle slot receiving said hypodermic needle to permit said cap to extend substantially around said hypodermic needle and restrict access to said hypodermic needle when said cap is in said covered position.

6. A safety needle assembly for use on a syringe, said assembly comprising:
    a tube being configured to receive an end of the syringe and being in fluid communication with the syringe, said tube including a base portion and a transfer portion, said base portion being configured to engage the end of the syringe and fluidly couple said transfer portion to the syringe;
    a hypodermic needle being fluidly coupled to and extending away from a distal end of said transfer portion with respect to said base portion;
    a cap being selectively positioned over and covering said hypodermic needle, said cap being positioned in either a covered position or an exposed position, said covered position being defined by said cap being positioned over a portion of said tube and a free end of said hypodermic needle to inhibit access to said hypodermic needle, said exposed position being defined by said cap being positioned away from said hypodermic needle to expose said free end of said hypodermic needle, said cap including a first end removably coupled to said tube and a second end extending beyond said free end of said hypodermic needle in a direction away from said tube when said cap is in said covered position, said cap having a channel therein positioned adjacent to said first end and having a size and shape configured to receive a portion of said tube when said cap is in said covered position, said cap having an elongated needle slot therein extending from said channel and towards said second end, said hypodermic needle slot receiving said hypodermic needle to permit said cap to extend substantially around said hypodermic needle and restrict access to said hypodermic needle when said cap is pivoted into said covered position;

a hinge being coupled between said tube and said cap to permit pivoting of said cap with respect to said tube, said hinge including;
  a stanchion being integrally coupled to said base portion of said tube and extending substantially orthogonally outwardly from said tube;
  a pair of pivot plates extending outwardly from sides of said stanchion and extending substantially perpendicular to a longitudinal axis of said tube, said plates lying in a plane orientated approximately perpendicular to a longitudinal axis of said hypodermic needle; and
  a pair of arms being integrally coupled to said cap adjacent said first end of said cap, said arms being positioned in a spaced relationship to permit said stanchion to be positioned between said arms, each of said arms having an aperture extending therethrough, each of said pivot plates extending through one of said apertures to permit said arms to pivot around said pivot plates and thereby allow said cap to pivot with respect to said tube, each of said arms including a locking slot extending therethrough, each of said locking slots extending into one of said apertures, each of said locking slots receiving one of said pivot plates when said cap is in said closed position to inhibit rotation of said cap and inadvertently exposing said hypodermic needle when said cap is in said covering position, said arms being moved toward said longitudinal axis of said hypodermic needle and toward said tube such that said plates align with and are received by an associated one of said locking slots.

* * * * *